United States Patent
Nardolillo et al.

(10) Patent No.: US 6,471,951 B1
(45) Date of Patent: Oct. 29, 2002

(54) EYEBROW PENCIL WITH AGGLOMERATED PIGMENTS

(75) Inventors: Irene Nardolillo, Northport; Tatyana Rachel Tabakman, Brooklyn, both of NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/526,364

(22) Filed: Mar. 16, 2000

Related U.S. Application Data

(63) Continuation-in-part of application No. 09/303,233, filed on Apr. 30, 1999.
(51) Int. Cl.[7] .......................... A61K 7/021; A61K 6/00; A61K 7/00
(52) U.S. Cl. ........................................ 424/63; 424/401

(58) Field of Search ........................... 424/63, 400, 401

(56) References Cited

U.S. PATENT DOCUMENTS 5,011,680 A * 4/1991 Suzuki et al. ................. 424/64
5,382,433 A * 1/1995 Pahlck et al. ............... 424/401

FOREIGN PATENT DOCUMENTS

DE         19856432 A1 * 6/2000

* cited by examiner

Primary Examiner—Thurman K. Page
Assistant Examiner—S. Howard
(74) Attorney, Agent, or Firm—Karen A. Lowney

(57) ABSTRACT

The invention relates to a cosmetic pencil which comprises a cosmetic base in which is dispersed at least one agglomerated pigment, in a pencil carrier.

29 Claims, 2 Drawing Sheets

EYEBROW PENCIL WITH AGGLOMERATED PIGMENTS

Figure 1A:
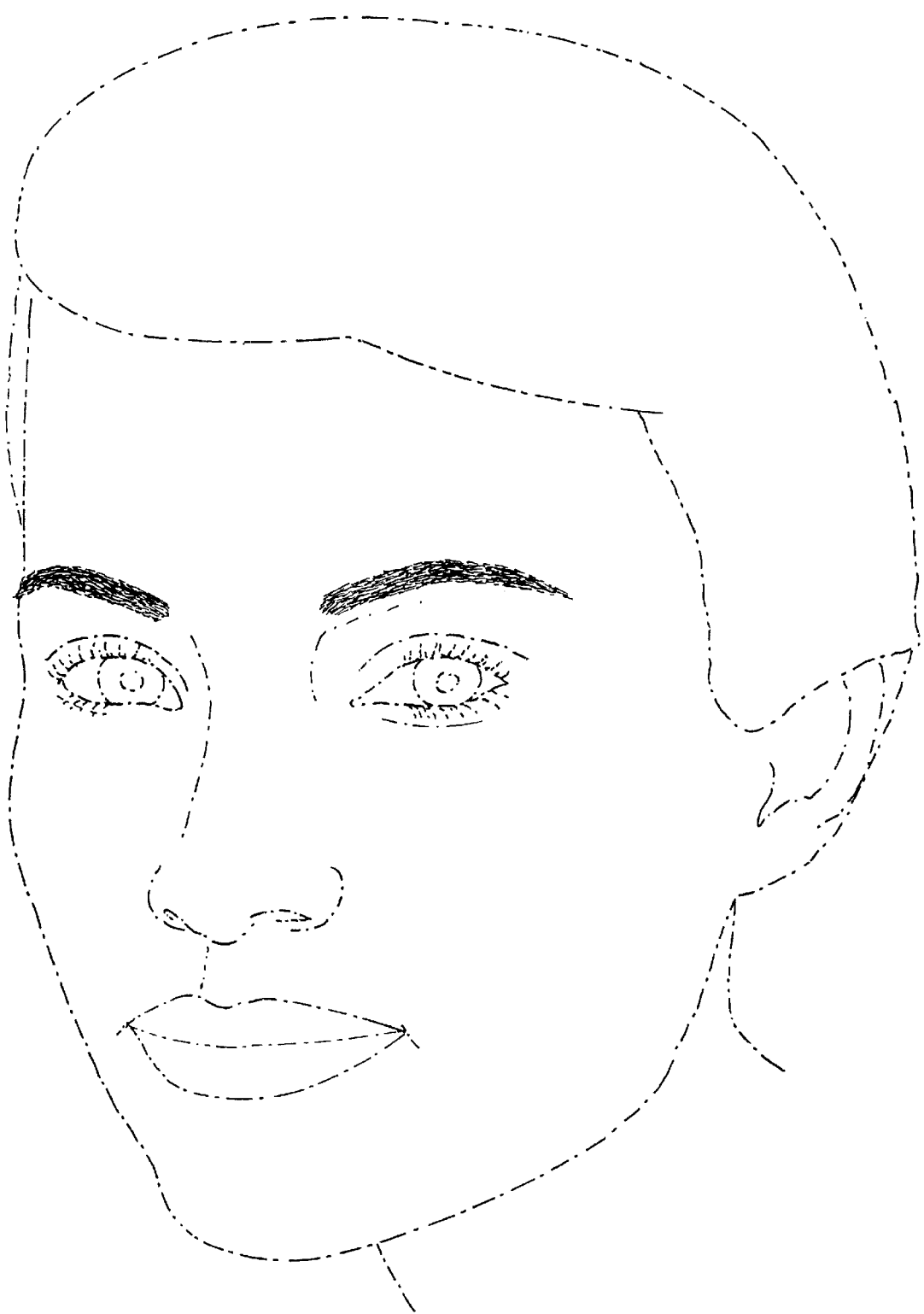

This application is a continuation-in-part of U.S. application Ser. No. 09/303,233, filed Apr. 30, 1999.

FIELD OF THE INVENTION

The invention relates to cosmetic compositions. More particularly, the invention relates to cosmetic composition for use in eyebrow pencils.

BACKGROUND OF THE INVENTION

The use of pigmented materials to ornament the eye area is a practice that goes back at least to ancient Egyptian times. It was not uncommon at that time for women, and even men, to adorn their eyelids, eyebrows and lashes with kohl, a black powder, which was probably at the time made from galena or lead sulfide. The habit was so popular that people often shaved their eyebrows, in order to replace them with heavily drawn kohl imitations.

The love of eye ornamentation was not limited to Egypt, but rather was widespread in the ancient world. Kohl continued to be the eye cosmetic of choice, but by Roman times had come to be made of antimony sulfide. Nonetheless, the habit of emphasizing or replacing the natural brows with a darker, less natural line continued throughout the centuries. Although in recent times kohl eventually was replaced by synthetic, but safer, pigmented cosmetics, even in the 20th century women have often plucked or even shaved their eyebrows, and filled in the natural brow line with colored cosmetic pencils.

As the world prepares to enter a new century, however, the trend in eyebrow ornamentation has returned back to the natural look. It is now uncommon to see the unnatural high arch of an eyebrow thought to be so attractive in earlier years, even in relatively modern times. Notwithstanding this return to nature, brow pencils are still much in demand, frequently being used to compensate for what nature may have neglected. Such pencils are now commonly used to provide a more natural and attractive shape to the brow, or to fill in sparse areas of the brow, rather than to replace it with another image entirely. In this regard, modern eyebrow pencils have not kept up with the trend. Most commercially available pencils consist of a solid wax base in which have been uniformly dispersed one or more pigments. Such pencils do provide good color to the brow. However, the resulting image frequently hearkens back to ancient times: the color can only be applied to the brow in a solid single-color line, which confers a now-unstylish harsh and unnatural look to the brow, which is unacceptable to most women seeking a natural look, since no natural brow consists of a single color, nor are the natural lines ever uniform or unbroken.

Certain types of more recent brow pencils have attempted to overcome the problem by utilizing different colors in a single pencil, thereby offsetting the hard look of the dominant single color line by the presence of other colors. While the presence of other colors does assist in lending a softer, more natural look, the presence of the single unbroken line remains, and thus, such pencils still do not completely resolve the problem of creating a brow with an uncontrived appearance.

Clearly, there is a need for a brow pencil that will effectively fill in gaps or gently shape the brow, and yet will leave the user with a soft, naturally appearing eyebrow. The present invention now provides such a product.

SUMMARY OF THE INVENTION

The invention relates to cosmetic composition for use in a cosmetic pencil comprising a wax base into which is distributed at least one agglomerated pigment. The pigment is incorporated into the wax base in such a way so as to substantially avoid breaking down the agglomeration, resulting in a non-uniform dispersal of the color from the pigments throughout the pencil. The resulting composition, rather than being uniformly colored throughout the base, has discrete flecks of pigment distributed through the base; when incorporated into a pencil, and applied to the skin, preferably in the eyebrow area, the composition produces wisps of color from the agglomerated pigment on the skin, approximating the appearance of brow or other natural hairs, thereby providing a more natural look than traditional brow pencils.

The invention also provides a method for making an eyebrow pencil comprising combining a wax base with at least one agglomerated pigment; mixing under conditions sufficient to achieve uniform distribution of the pigment throughout the wax base, but insufficient to permit deagglomeration of the pigment and homogeneous coloring of the wax base; and incorporating the combined wax base and pigment into an appropriate pencil carrier.

The invention also relates to a method of coloring the eyebrow area which comprises applying to the eyebrow area a pencil as described above.

BRIEF DESCRIPTION OF THE INVENTION

Figure 1B:
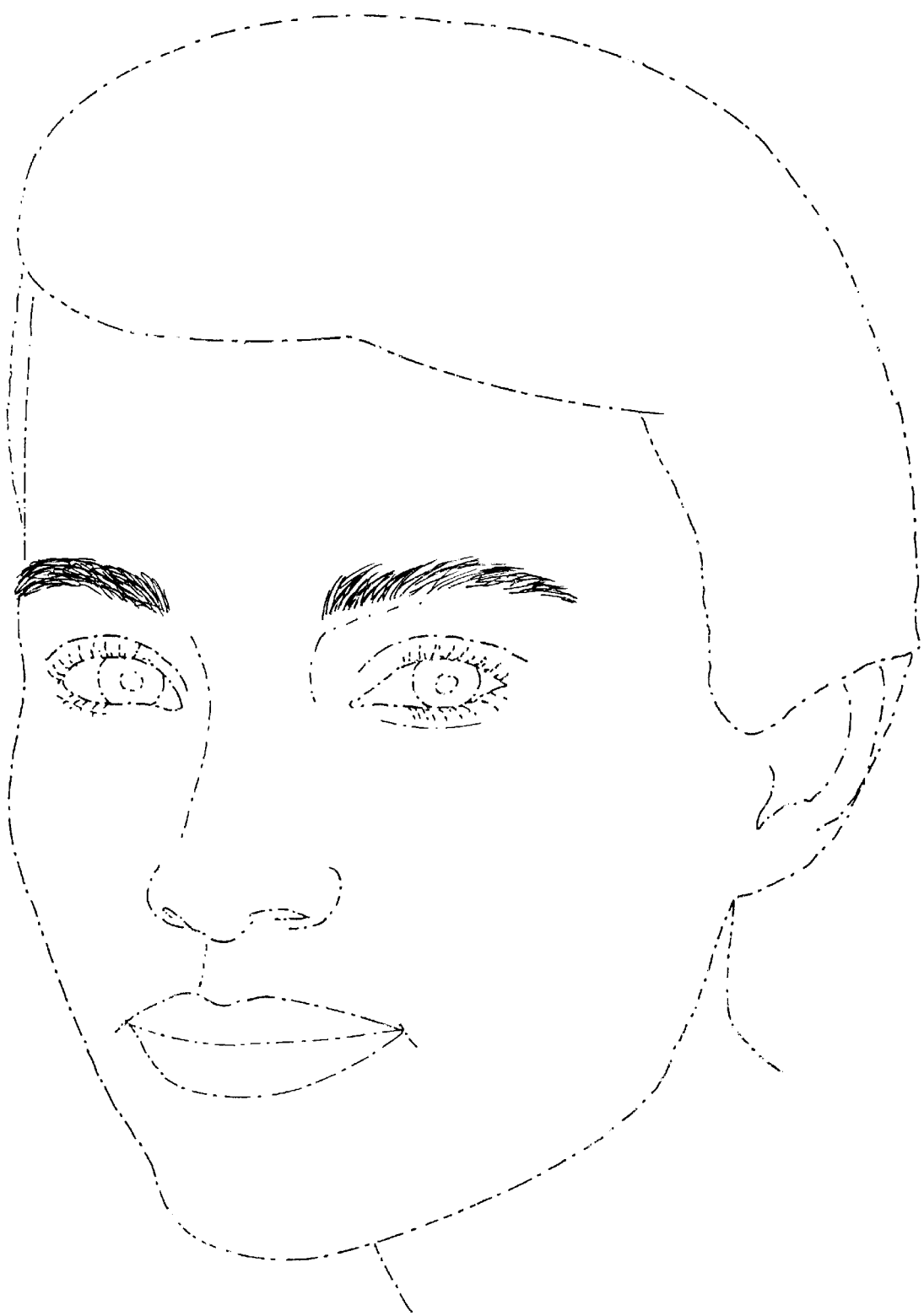

FIG. 1 shows a comparison of the appearance of (A)brows to which a traditional brow pencil has been applied, and (B)brows to which a pencil of the present invention has been applied.

DETAILED DESCRIPTION OF THE INVENTION

The typical brow pencil is prepared with a cosmetic base, frequently a wax base, which is first melted, and to which the chosen colorants then are added. The combined base and colorants are then thoroughly mixed, so as to completely distribute the color from the colorants throughout the base; in other words, the base becomes substantially homogeneously colored by the dispersed colorants. The pigments used in such pencils can be either organic or inorganic, but in all cases, it is generally preferred that the colorant particles start out small, usually less than 1 $\mu$, so as to facilitate their mixing into the base to achieve a uniform single color.

In contrast, the cosmetic of the present invention, while employing a standard cosmetic pencil base, utilizes an agglomerated or granular inorganic pigment. By "agglomerated" or "granular" pigment in the present specification and claims is meant an insoluble pigment with a particle size of at least about 10 $\mu$, up to 1000 $\mu$, but preferably in the range of from about 100 to about 800 $\mu$, more preferably from about 400 to about 600 $\mu$. For the purposes of the present invention, such pigments must be of such firm consistency and have such mechanical stability that the particles are not easily broken down and the color uniformly distributed throughout the pencil base by the process of mixing them into the base. In general, such agglomerated or granular pigments are prepared by binding and/or compaction of smaller pigment particles, normally in the presence of a binder. Such pigments have frequently been made in order reduce the dust normally produced by handling of the smaller particle size pigments. Granular pigments of this type are commercially available from Whittaker, Clark, & Daniels (Plainfield, N.J.) and Elementis Pigments (Easton, Pa.). The pigments may be based on any cosmetically acceptable insoluble or substantially insoluble pigments. Most frequently, the pigments are based on metallic oxides, such as yellow, black, brown, or red iron oxides, white titanium dioxide, chromium oxide or a mixture of any combination thereof. However, the agglomerated or granular pigment may also be based on lakes, pigments formed by the precipitation and absorption of organic dyes on an insoluble base, such as alumina, barium, or calcium hydrates. The most preferred agglomerated particles are iron oxides and titanium dioxides. The agglomeration of the pigment particles permits them to substantially retain their integrity during the mixing process, thereby resulting in visually discrete granules or particles throughout the cosmetic base of the pencil. The amount of particles employed is not particularly critical, and can be varied; however, these particles will normally be used in an amount of about 0.1 to about 10%, more commonly from about 1 to about 5%, by weight of the total composition.

The pencil may use any type of cosmetic base that is standard in the art for the making of cosmetic pencils or sticks. Most commonly, however, the base will be a wax base, i.e., comprising one or more waxes. The term "waxes" in the present specification and claims includes waxes in the traditional sense, i.e., those plant, animal or mineral waxes containing primarily esters of higher fatty acids and alcohols, free higher acids and alcohols, and saturated hydrocarbons; examples of such traditional waxes include, but are not limited to, carnauba wax, candelilla wax, beeswax, synthetic wax, shellac wax, spermaceti, lanolin wax, ozokerite, bran wax, ceresin wax, bayberry wax, paraffin, rice wax and jojoba wax. However, "waxes" will also be understood to include other non-traditional wax-like materials, i.e., having a wax-like, hard, brittle, relatively non-greasy texture, including, but not limited to, various fatty alcohols, fatty acids, fatty esters, hydrogenated oils and glycerides, polyethylenes, polyethylene glycols, and sterols as well as synthetic resinous products such as silicone waxes. Normally, the wax component of the base will constitute from about 5 to about 50%, more preferably about 15 to about 45%, by weight of the total pencil cosmetic composition.

The wax base composition also will typically contain one or more oils, which serve to soften the wax. The oil may be any cosmetically acceptable oil, but preferably, the oil component will primarily be a non-volatile oil. Useful oils materials include, but are not limited to, hydrocarbons, such as squalane, petrolatum, petrolatum, $C_{8-9}$ isoparaffin, $C_{11-12}$ isoparaffin, isohexadecane, isododecane, and hydrogenated polyisobutene; plant oils, such as castor oil, coconut oil, corn oil, jojoba oil, cottonseed oil, soybean oil, walnut oil, wheat germ oil, sunflower seed oil, palm kernel oil, calendula oil; C10–18 triglycerides, lanolin and lanolin derivatives, illipe butter, shea butter; esters having the formula RCO—OR' wherein RCO represents a carboxylic acid radical and OR' represents an alcohol residue, such as isodecyl neopentanoate, tridecyl octanoate, cetyl palmitate, cetyl octanoate, cetyl stearate, cetyl myristate, isopropyl palmitate, isopropyl myristate, polyglyceryl-2-isostearate, neopentyl glycol distearate, isodecyl oleate, decyl isostearate, diisopropyl sebacate, PEG-4 diheptanoate, dioctyl malate, and isohexyl neopentanoate; fatty alcohols, such as lanolin alcohol or oleyl alcohol; and silicone oils, such as cyclomethicone, dimethicone, cetyl dimethicone, lauryl trimethicone, and dimethiconol. The amount of oil used will depend on the desired texture of the final product, but will generally be in the range of from about 10 to about 40% by weight of the composition.

The base may also comprise additional non-colorant powder or filler materials, such as are frequently used in cosmetic compositions. Examples of such powders or fillers include mica, boron nitride, silica, talc, calcium carbonate, starch, nylon, kaolin, bismuth oxychloride, or coated versions of each of these, for example, with lecithin, silicones, amino acids, fatty acids, fatty alcohols, or metallic soap coatings. These fillers may also be present in an amount of about 10 to about 50% by weight.

It is ordinarily intended that the base of the pencil remain uncolored, i.e., does not contain any colorant other than the agglomerated pigments, so that it will blend easily into the skin of the user. However, in some circumstances it may be desirable to incorporate a small amount of additional, non-agglomerated pigment, so as to approximate a skin tone for the background of the agglomerated pigment. In such a case, the base may also contain other inorganic pigments, such as non-agglomerated iron oxides, titanium dioxide, chromium oxide, or ultramarine or organic pigments; the inorganic pigments are particularly preferred. These additional non-agglomerated pigments, if used, should be used in such as way as to confer so little color as to not obscure the effect of the agglomerated pigment on the skin; therefore, the amounts of these pigments will ordinarily be no more than about 1 to about 5%.

The general process by which the pencil composition is prepared is substantially the same as used in the preparation of any traditional pencil, provided the method used does not involve such strenuous mixing so as to contribute to the breakup of the agglomerated particles. In brief, in one embodiment, the wax is melted and combined with any other liquid components; to this combination is added any additional components other than the granular or agglomerated pigment, and all are mixed well. Only toward the end of the mixing process is the primary pigment added, and mixed for a short period of time, so as to evenly distribute the particles throughout the base, but so as not to break them up and cause the color to be dispersed uniformly through the base. The molten base is then poured into wooden pencil cases, and allowed to cool.

The principle use of the pencils of the invention will be as an eyebrow pencil, to fill in or emphasize the original brow line. However, the pencil can be used in any situation in which simulation of hair would be desirable, such as filling in bare spots in a mustache or beard, or on a scalp, along a hairline. In a further embodiment, the pencil can also have incorporated a hair growth stimulating agent, to promote growth of hair in areas of a brow, beard, mustache or hairline where hair growth is sparse. Examples of useful such materials for incorporation include, but are not limited to, minoxidil, and herbal/botanical extracts or oils, such as *Paeonia suffructosa* Andrews, *Pilocarpus pennatifolius* (jaborandi extract), *Salvia officianalis* or sclarea (sage), *Urtica dioica*(nettle), *Cinchona pubescens* or *succirubra* (red cinchona), *Tectona grandis* (teak tree oil), *Hypericum perforatum* (St. John's wort flower or extract), and the Chinese medical mixture comprising rehmanniae radix, safflower, peony root, angelicae radix, glycyrrhiza radix, peppermint, pinnatifida DC, pepper, and malay camphor. The use of such materials is widely known, and they may be used, alone or in combination, in the amounts typically used as effective in tonics and other hair growth products. The active component or components will be added to the cosmetic base at substantially the same time as the addition of the granular pigments.

The invention is further illustrated by the following non-limiting examples.

EXAMPLES

Example 1

This example illustrates a composition of the present invention, and a method of making same.

Granular pigments are prepared as follows: a high melting point polyethylene, Performalene PL, is melted at 95° C., and combined with an iron oxide or titanium dioxide pigment at a ratio of about two parts pigment, to one part polyethylene. The combined polyethylene and pigment are mixed to uniformity, and allowed to cool to a dry mass. The dry mass is then placed in an Osterizer, and ground into small but visually discrete particles of about 500–600 μ in size.

A wax-based pencil composition of the following formula is prepared.

| Material | Weight Percent |
| --- | --- |
| brown iron oxide | 1.00 |
| polyethylene | 1.67 |
| pure oxy black | 1.00 |
| titanium dioxide | 1.33 |
| hydrogenated vegetable oil | 21.00 |
| hydrogenated coco-glycerides | 17.00 |
| caprylic/capric triglycerides | 9.00 |
| beeswax | 4.00 |
| hydrogenated lanolin | 3.00 |
| dimethicone, 5 cs | 1.00 |
| kaolin | 40.00 |

The wax base components, both solid and liquid, are melted together at about 92–95° C., with kaolin being added in last. The wax base so prepared is allowed to cool to 75–80° C., and is then combined with the premade granular pigment phase. The two phases are melted down together, and combined by mixing with a Lightnin' mixer; when the granular pigment is distributed evenly, but still substantially whole, throughout the base, the composition is poured into a wooden pencil case.

A second formula is prepared is prepared similarly using commercially available granular pigments:

| Material | Weight Percent |
| --- | --- |
| ceresin | 12.35 |
| beeswax | 1.15 |
| carnauba wax | 8.50 |
| propylparaben | 0.10 |
| lanolin (anhydrous) | 11.50 |
| diisostearyl malate | 16.425 |
| polyglyceryl-2-triisostearate | 5.70 |
| squalane | 15.425 |
| sericite | 12.425 |
| talc | 12.425 |
| granular black oxide (Whittaker, Clark & Daniels) | 3.00 |

What we claim is:

1. A cosmetic pencil comprising a cosmetic pencil base in which is distributed at least one agglomerated pigment, in a pencil carrier.

2. The pencil of claim 1 in which the pigment is an insoluble inorganic pigment.

3. The pencil of claim 1 in which the pigment is selected from the group consisting of iron oxides and titanium dioxide.

4. The pencil of claim 1 in which the pigment has an average particle size of from about 10 to about 1000 μ.

5. The pencil of claim 1 in which the pigment has an average particle size of about 200 to about 800 μ.

6. The pencil of claim 1 in which the pigment has an average particle size of about 400 to about 600 μ.

7. The pencil of claim 1 in which the cosmetic base is a wax base comprising from about 5 to about 50% of one or more waxes.

8. The pencil of claim 7 in which the base comprises from about 15 to about 45% of one or more waxes.

9. The pencil of claim 1 in which the base comprises one or more oils in an amount of about 10 to about 40%.

10. The pencil of claim 1 in which the base comprises one or more cosmetic powders or fillers in an amount of about 10 to about 50%.

11. The pencil of claim 1 which also comprises a hair-growth stimulating agent.

12. A cosmetic pencil comprising a wax base in which is distributed at least one agglomerated insoluble inorganic pigment, in a pencil carrier.

13. The pencil of claim 12 which comprises from about 5 to about 50% of one or more waxes, and at least one metallic oxide agglomerated pigment.

14. The pencil of claim 13 in which the metallic oxide is an iron oxide, titanium dioxide, or a combination thereof.

15. The pencil of claim 12 which comprises from about 10 to about 40% of one or more oils.

16. The pencil of claim 12 which comprises from about 10 to about 50% of one or more cosmetic powders or fillers.

17. The pencil of claim 12 in which the pigment has an average particle size of about 200 to about 600 μ.

18. The pencil of claim 12 which comprises about 15 to about 45% of one or more waxes, about 1 to about 5% of at least one iron oxide or titanium dioxide agglomerated pigment having an average particle size of about 200 to about 600 μ, about 10 to about 40% of one or more oils, and about 10 to about 50% of one or more fillers.

19. The pencil of claim 12 in which the agglomerated pigment has an average particle size of about 500 to about 600 μ.

20. The pencil of claim 12 which also comprises a hair-growth stimulating agent.

21. A method for making a cosmetic pencil comprising combining a cosmetic pencil base with at least one agglomerated pigment; mixing the base and pigment under conditions sufficient to achieve uniform distribution of the pigment throughout the base, but insufficient to permit substantial deagglomeration of the pigment and homogeneous coloring of the base, to form a uniform mixture; and incorporating the mixture into a pencil carrier.

22. The method of claim 21 in which the agglomerated pigment is an inorganic pigment.

23. The method of claim 22 in which the agglomerated pigment is an iron oxide, titanium dioxide, or a combination thereof.

24. The method of claim 22 in which the agglomerated pigment has an average particle size of from about 10 to about 1000 μ.

25. The method of claim 23 in which the agglomerated pigment has an average particle size of from about 200 to about 600 μ.

26. The method of claim 25 in which the agglomerated pigment has an average particle size of from about 500 to about 600 μ.

27. The method of claim 21 in which the cosmetic base is a wax base containing from about 5 to about 50% of one or more waxes.

28. The method of claim 27 in which the wax base is melted, and the agglomerated pigments are added to the melted base.

29. The method of claim 21 which also include the step of incorporating into the pencil a hair-growth stimulating agent.

* * * * *